Figure 1:
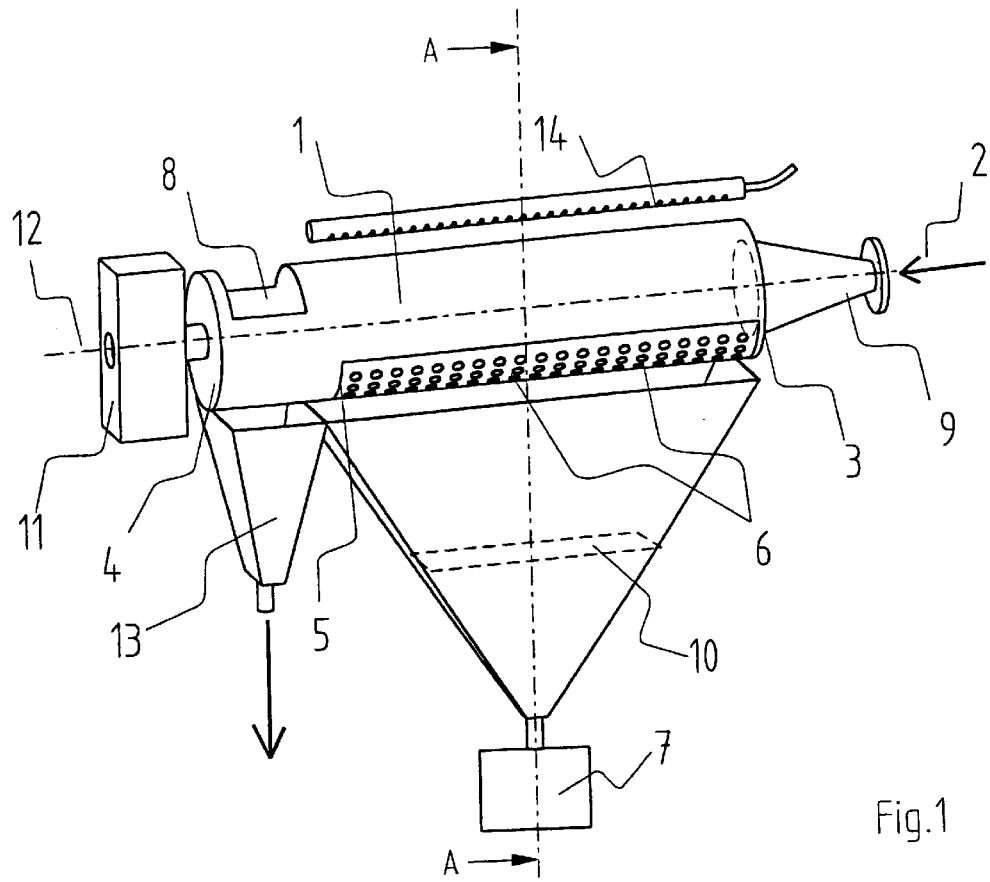

United States Patent [19]
Mann et al.

[11] Patent Number: 6,148,679
[45] Date of Patent: Nov. 21, 2000

[54] SAMPLE FLOW CONTROL MEMBER

[75] Inventors: Kari Mann; Jari Moilanen, both of Espoo, Finland

[73] Assignee: Outokumpu Oyj, Espoo, Finland

[21] Appl. No.: 09/349,220

[22] Filed: Jul. 7, 1999

[30] Foreign Application Priority Data

Jul. 9, 1998 [FI] Finland .................................... 981581

[51] Int. Cl.⁷ .................................................. G01N 1/00
[52] U.S. Cl. ..................... 73/863.51; 73/863.24
[58] Field of Search ........................ 73/863.23, 863.24, 73/863.51, 863.56, 863.57, 863.86, 864.81; 251/304, 310, 309, 311; 137/628, 862, 613, 614.11, 561 A; 141/130, 134

[56] References Cited

U.S. PATENT DOCUMENTS

| | | |
|---|---|---|
| 2,807,961 | 10/1957 | Grimes . |
| 4,574,645 | 3/1986 | Allen et al. .......................... 73/863.56 |
| 4,628,962 | 12/1986 | Pezzarossi ................................ 251/310 |
| 4,779,466 | 10/1988 | Ramsner et al. ...................... 73/863.24 |
| 4,816,155 | 3/1989 | Ivan ...................................... 73/836.81 |
| 4,840,074 | 6/1989 | Jessop .................................... 73/864.81 |
| 4,946,650 | 8/1990 | Röthele . |
| 5,005,432 | 4/1991 | Faulkner .............................. 73/863.86 |
| 5,021,126 | 6/1991 | Gwin et al. . |
| 5,369,981 | 12/1994 | Merz et al. ........................... 73/863.23 |

FOREIGN PATENT DOCUMENTS

| | | |
|---|---|---|
| 3543758 | 9/1986 | Germany . |
| 1012077 | 4/1983 | Russian Federation . |
| 605845 | 7/1948 | United Kingdom . |

*Primary Examiner*—Robert Raevis
*Attorney, Agent, or Firm*—Smith-Hill and Bedell

[57] ABSTRACT

The invention relates to a sample flow control member to be used particularly in a continuously operated analysis of liquid or slurry-like materials, said control member being provided with members for selectively conducting the sample flow to an analyser. According to the invention, the control member (1, 21, 41) is installed in an essentially horizontal position and provided with at least one moving member (11, 28, 42) in order to turn the control member (1, 21, 41) around its rotation axis (12, 29, 48) in order to selectively conduct the sample flow to at least one analyser (7, 27; 44, 46) through at least one aperture (5, 25, 49) provided in the wall of the control member (1, 21, 41).

13 Claims, 2 Drawing Sheets

SAMPLE FLOW CONTROL MEMBER

The present invention relates to a sample flow control member which is used particularly for a continuously operated selective analysis in industrial processes dealing with liquid and slurry-like materials, wherein from the different process stages, samples are removed in turn to be measured in a centralised analyser.

In industrial processes, the conducting of samples removed from the various process stages to the analyser is usually carried out by means of a sample multiplexer. In order to achieve a reliable accuracy of analysis as regards the flow of the material to be analysed, the primary sample flow must be sufficiently large, and it must be continuously maintained, or the sample lines must be washed in between each sampling sequence. Generally the material flow passing through the analyser is maintained on an essentially constant level, and essentially smaller than the primary sample flow. Therefore the sample multiplexer usually contains a tank, the surface level whereof is maintained by feeding new sample into the tank whenever the tank surface drops. Another purpose of the tank is to remove any air that has entered along with the sample through the open liquid surface. This type of sample multiplexer is described for instance in the FI patent 77,121, where the sample flow passes in the vertical direction, and the sample to be analysed is fed into the sample tank by deviating the head of the sampling tube for example by means of a pneumatic cylinder from the bypass flow position to the tank. In the sample feeding spot of the sample multiplexer, there can be installed a scrap screen for preventing any scrap that has come along with the sample from entering the analyser. The cleaning of this scrap screen is one of the most frequently performed maintenance operations required by the analyser. The drawback of the sample multiplexer according to the FI patent 77,121 is the large volume of space needed in the vertical direction, which also increases the pumping height of the sample flow. Moreover, the scrap screen that is possibly installed at the head of the sample tube tends to be blocked by fibrous scrap.

The object of the present invention is to eliminate some of the drawbacks of the prior art and to achieve an improved sample flow control member that requires less maintenance, which sample flow control member is installed essentially in the horizontal position in the primary sample flow, so that the primary sample flow can be conducted, essentially continuously, via the sample flow control member at the same time as scrap material is removed from the sample flow before it has entered the analyser. The essential novel features of the invention are apparent from the appended claims.

According to the invention, the sample flow control member is formed of a part that is advantageously essentially tubular in cross-section and can be turned by means of at least one moving member around the longitudinal axis thereof. In cross-section, said part can also be essentially angular or essentially oval-shaped. A sample flow control member that is ready for operation is installed in an essentially horizontal position, and in the wall of the part constituting the sample flow control member, there is advantageously formed at least one aperture in order to selectively conduct the sample flow into at least one analyser. The number of the apertures provided in the wall of the sample flow control member and guiding the sample flow into the analyser can be several, and they can be positioned both adjacently and successively with respect to the flowing direction of the sample flow. Moreover, the aperture or apertures that guide the sample flow into the analyser are provided with a screen-like member in order to remove any waste material contained in the sample flow before the sample flow reaches the analyser. Said screen-like member is attached to the aperture so that when turning the control member, the screen-like member moves along with the aperture. Advantageously the member filtering the sample flow can also be formed by a number of perforations leading to the analyser, the diameter of said perforations being made such that any particles defined to be too large for the sample flow are filtered away. Thus it is not necessary to use a separate screen-like member.

According to a preferred embodiment of the invention, in addition to the aperture conducting the flow to the analyser, in the wall of the part there also is made at least one aperture for conducting the sample flow back to the main material flow. In that case the first end of the part that constitutes the sample flow control member is advantageously essentially open in the sample flowing direction, whereas the second end of the part constituting the sample flow control member is essentially closed in the sample flowing direction. According to the embodiment in question, the sample flow is conducted into the control member via the open end and discharged from the control member either through the aperture leading to the analyser or through the aperture leading back to the main material flow.

The sample flow control member according to the invention can also be constructed so that both ends of the part constituting the sample flow control member are open, in which case the sample flow is fed to the control member at the first end in relation to the flowing direction, and it is discharged through the second end in relation to the flowing direction. The sample flow going to the analyser passes through an aperture provided in the wall of said part, and through a screen-like member or through an array of perforations forming the screen-like member and provided in said aperture.

When the sample flow control member according to the invention is used for guiding the sample flow, the control member is first set in an essentially horizontal position, while the angle of inclination is within the range of 0–10 degrees, advantageously within the range of 0–3 degrees. When it is desired to conduct a sample flow to the analyser through the control member, the aperture formed in the control member wall and provided with a screen-like member, or the array of perforations forming the screen-like member, are by means of a moving member set in a position where the aperture is nearest to the analyser, in the bottom part of said part with respect to the longitudinal rotation axis of the control member. Now a sample flow is conducted into the control member via the end of the part constituting the control member, and when the sample flow proceeds to the aperture provided with the screen-like member, the sample flow is discharged from the control member, downwardly towards the analyser. The undesirable waste material contained in the sample flow remains in the screen-like member provided at the aperture. When the screen-like member or the perforations constituting the screen-like member should be cleaned, or when the sample flow should for some other reason be conducted back to the main material flow, the part constituting the control member is turned, so that the aperture provided with the screen-like member is moved, by means of the moving member, to a position where the sample flow cannot anymore enter the analyser through the aperture, at least not to any essential amount. Now the waste material left in the screen-like member is dropped back to the main material flow, which is conducted out of the control member through the open end of the control member or through the aperture formed in the wall of said part. The discharge of the waste material from the screen-like member can be made more effective by installing at least one cleaning material nozzle outside the part constituting the control member, in the immediate vicinity of said part, advantageously essentially at the aperture provided in the wall. When necessary, cleaning liquid is advantageously fed to the screen-like member via the cleaning agent nozzle, and the waste material is discharged from the control member along with said cleaning liquid. The cleaning agent nozzle and the cleaning agent fed to the control member wherethrough can also be used for cleaning the control member itself.

The sample flow control member according to the invention is installed in an essentially horizontal position while the angle of inclination is 0–10 degrees, advantageously 0–3 degrees, so that the second end of the part constituting the control member is set lower than the first end, when seen in the flowing direction. If the sample flow control member according to the invention is installed so that the control member forms an angle of inclination with the horizontal plane, the control member can also be installed so that the first end of the control member is set lower than the second end, when seen in the flowing direction. Because the control member according to the present invention is installed in an essentially horizontal position, the need for space as well as the height required for lifting and pumping the material are reduced when compared with the prior-art vertical control member. Now the waste material is advantageously discharged from the control member, and the rest of the solids coming along with the sample flow are advantageously conducted to the screen-like member or, when a screen-like member is not used, to the bypass flow discharge tap of the control member.

The sample flow is conducted to the control member according to the invention so that the flowing rate when the sample flow enters the control member is advantageously within the range of 1–1.5 m/s. If necessary, the flowing rate is adjusted by using a speed moderator installed in front of the control member, when seen in the flowing direction. By means of an advantageous speed, the sample flow is made to flow essentially evenly to the aperture provided with a screen-like member or to the perforations constituting the screen-like member, which prevents the creation of splashes and keeps the waste material from being stuck in the sieve perforations.

The sample flow control member according to the invention can be utilised so that in one and the same sample flow, there are installed several control members side by side, in which case said control members can be used for instance so that one is in a cleaning position, while the other two are in a sample analysing position. Moreover, a number of the sample flow control members according to the invention can be installed adjacently, so that a sample flow is conducted to each control member from a different process stage. In that case only one control member is advantageously set in an position for operation, in order to conduct a sample to the analyser. Now the sample flows coming through the rest of the control members are conducted, via the bypass aperture, for instance back to the main material flow.

The sample flow control member according to the invention can also be utilised so that while turning the control member by means of the moving member between the various positions, the control member can also be adjusted to such positions that in one position, the sample flow is conducted to one analyser, and in another position, the sample flow is conducted to another analyser performing another task. It also is possible that the control member is installed, with respect to the conduit leading to the analyser, so that the sample flow, when being discharged from the control member, is divided into two or more sample flows and conducted to analysers performing different tasks. Among the analysers performing different tasks, one advantageously measures for instance the element contents of the material and the other measures the grain size.

Figure 2:
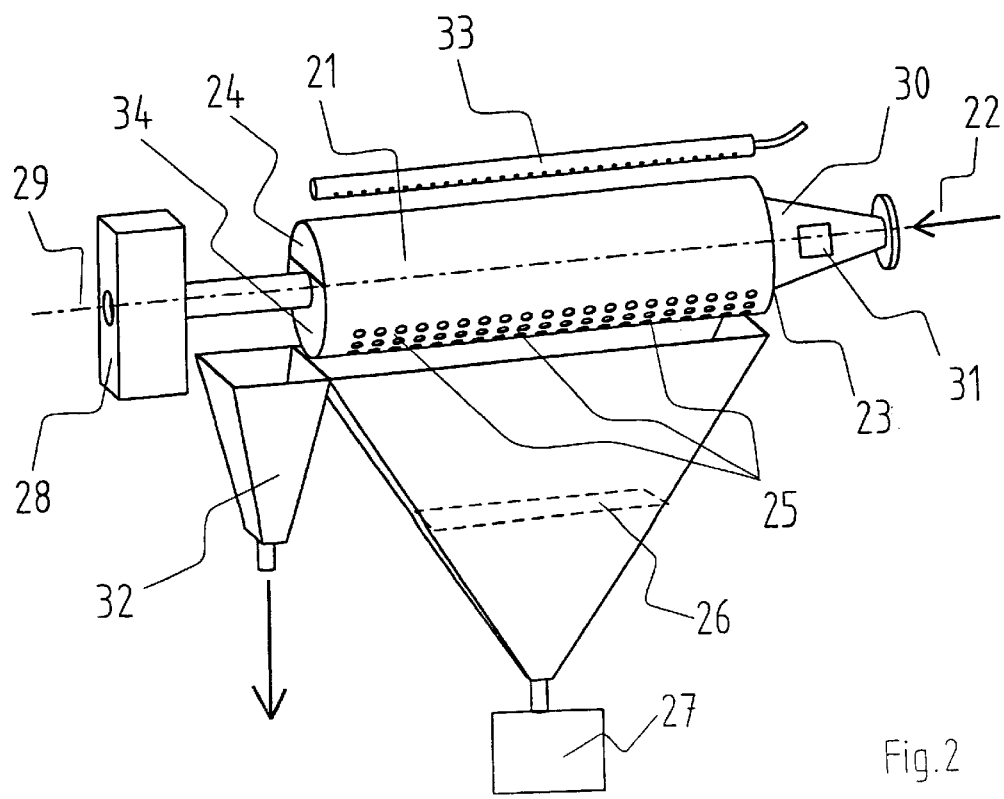
Figure 3:
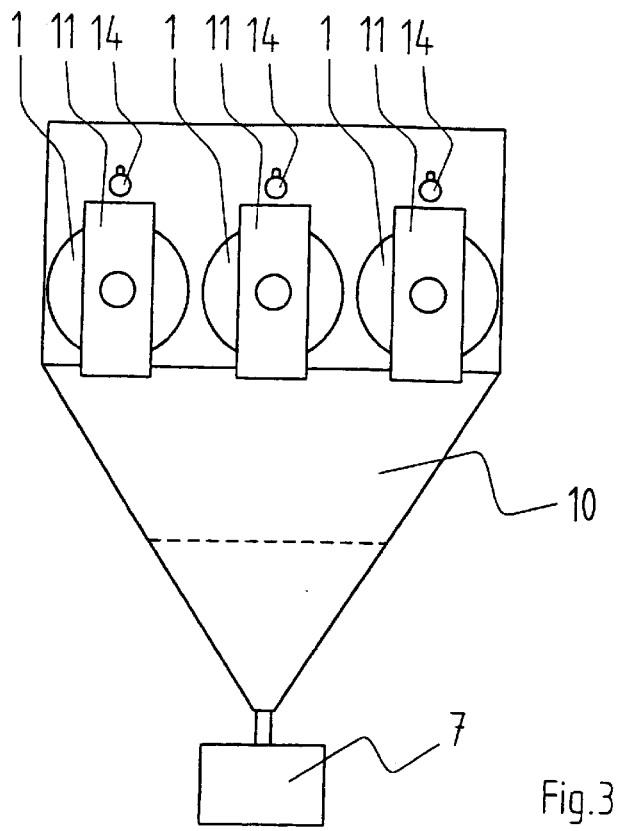
Figure 4:
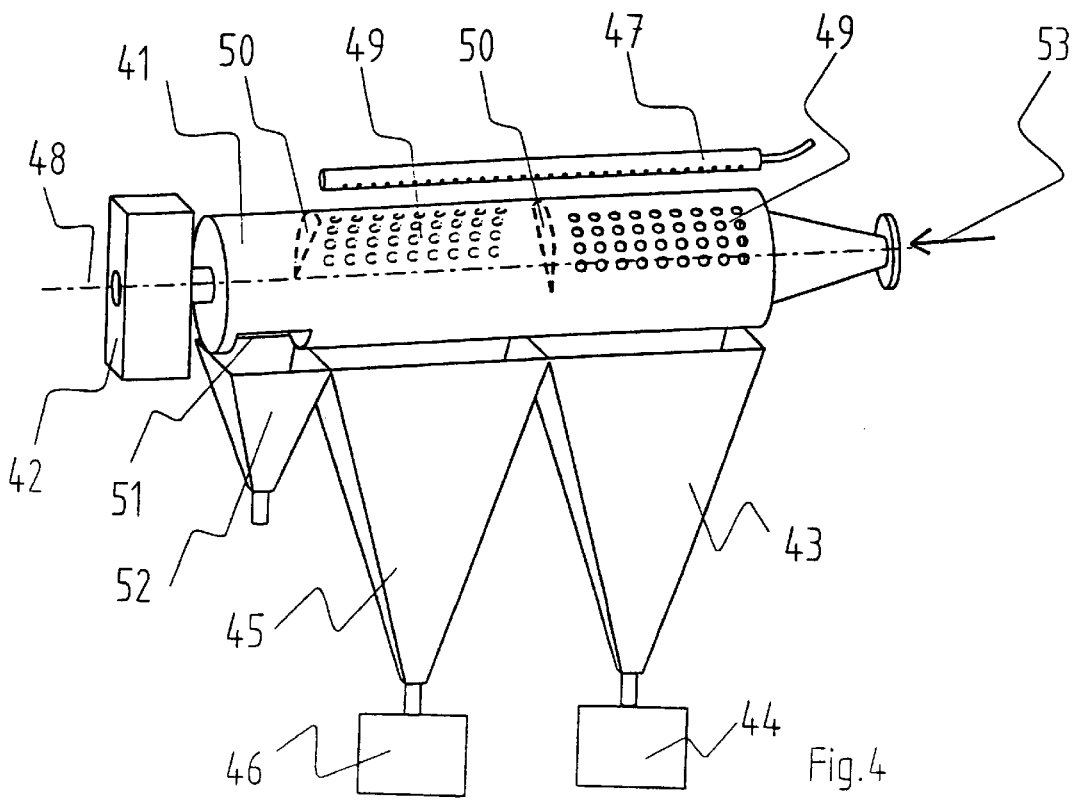

The invention is described in more detail below, with respect to the appended drawings, wherein FIG. 1 is a side-view illustration of a preferred embodiment according to the invention, FIG. 2 is a side-view illustration of another preferred embodiment according to the invention, FIG. 3 is a diagrammatic illustration of the embodiment of FIG. 1, seen in the direction A—A, when there are several control members installed adjacently, and FIG. 4 is a side-view illustration of a third preferred embodiment according to the invention.

According to FIG. 1, a sample flow control member 1 according to the invention is installed in an essentially horizontal position, so that the control member 1 forms an angle of about three degrees with respect to the horizontal plane, and that in the flowing direction 2 of the control member 1, the first end 3 is set higher than the second end 4. In the wall of the control member 1, there is formed an aperture 5 provided with a sieve 6. Via said aperture 5, the sample flow proceeding through the control member can be conducted to an analyser 7. Moreover, in the wall of the control member 1, there is formed an aperture 8 for guiding the sample flow past the analyser 7. In addition, the second end 4 of the control member 1 when seen in the flowing direction is closed, so that the sample flow cannot pass through the end 4.

When the sample flow control member 1 according to the invention is in operation, the sample flow is conducted, according to FIG. 1, to the control member 1 via the first end 3, when seen in the flowing direction. In order to conduct the flow to the control member 1, a feed conduit 9 is connected to the first end 3 of the control member when seen in the flowing direction. When necessary, the feed conduit 9 can be provided with a sample flow speed moderator, so that the flowing rate of the sample flow is advantageously adjusted to remain within the range of 1–1.5 m/s. While the control member 1 is in a position where the sample flow is conducted to the analyser 7, the sample flow coming from the feed conduit 9 is in the control member first conducted to the aperture 5 of the connecting part 10 of the analyser 7, and through the sieve 6 provided in said aperture 5, the desired sample flow is conducted to the analyser 7. When the sample flow should be interrupted in the analyser 7 or, for instance, in order to remove from the control member material that was contained in the sample flow but was left in the sieve 6, the control member 1 is turned, by means of a moving member 11, in relation to the longitudinal rotation axis 12 to a position where the aperture 8 provided in the wall of the control member 1 is located essentially in the bottom part of the control member 1, in the vicinity of the analyser 7. Via the aperture 8, the sample flow is now conducted, through the conduit 13, past the analyser 7. When the control member 1 is turned around the rotation axis 12, the aperture 5 that has lead the sample flow to the analyser 7 is set in a position where the sieve 6 provided in the aperture 5 can be cleaned. The sieve 6 is advantageously cleaned by means of a bypassing sample flow. The cleaning of the sieve 6 can be boosted by feeding cleaning liquid to the sieve 6 through nozzles 14 installed outside the control member 1, in the immediate vicinity thereof. The nozzles 14 can also be used for cleaning the control member 1 as such.

According to FIG. 2, the sample flow control member 21 according to the invention is installed in an essentially horizontal position, while the angle of inclination is about 3 degrees with respect to the horizontal plane, so that in the flowing direction 22 of the sample flow control member 21, the second end 23 is set higher than the first end 24. In the wall of the sample flow control member 21, there are made perforations 25 in order to conduct the sample flow from the control member 21 via a connecting part 26 to the analyser 27. In cross-section, the perforations 25 are made such that said perforations 25 also serve as a sieve for any waste material possibly contained in the sample flow, so that the waste material cannot damage the analyser 27. Moreover, the control member 21 is provided with a moving member 28, whereby the control member 21 can advantageously be turned around its rotation axis 29.

When using the embodiment according to FIG. 2, the first end 23 of the control member 21 when seen in the flowing direction 22 is provided with a flow conduit 30 in order to conduct the sample flow into the control member 21. Advantageously the conduit 30 is provided with a flow moderator 31, in which case the flowing rate of the sample flow when entering the control member 21 remains advantageously continuously within the range 1–1.5 m/s. When it is desired that the sample flow should enter the analyser 27, the perforations 25 provided in the wall of the control member 21 are, by means of the moving member 28, turned to a position where the sample flow can flow through the perforations 25 to the connecting part 26 and further to the analyser 27. In order to advantageously conduct the sample flow to the analyser 27, in succession to the perforations 25, in the flowing direction 22 of the sample flow, there is installed a flow stop member 34. In a case where the sample flow to the analyser 27 should be interrupted, for instance in order to clean the perforations 25, the control member 21 is turned by means of the moving member 28 to a position where the perforations 25 are essentially shifted to above the sample flow, and thus the sample flow is prevented from entering the analyser 27 as the effect of the flow stop member 34 ends. Now the sample flow is conducted through the latter end 24 of the control member 21, when seen in the flowing direction, to the connecting part 32 and further as a bypass flow past the analyser 27. In order to clean the perforations 25 and possibly the control member 21 at the same time, outside the control member 21, in the immediate vicinity thereof, there are installed nozzles 33 in order to feed cleaning liquid to the perforations 25.

In the illustration according to FIG. 3, there are arranged several control members 1 according to FIG. 1 adjacently, so that the control members 1 are either all connected to one and the same sample flow, in which case for instance the sample flow of one control member 1 to the analyser 7 is interrupted, or so that each of the control members 1 is connected to an individual sample flow, in which case only one control member 1 conducts the sample flow to the analyser 7.

In FIG. 4, there is illustrated a horizontally positioned control member 41, whereby the sample flow coming from the flowing direction 53 can be conducted to two separate analysers 44 and 46 by rotating the control member 41 by means of the moving member 42 around its rotation axis 48. In order to realise this, the control member 41 is provided with two perforation groups 49 forming a screen-like member, and while turning the control member 41, said perforation groups are set under the sample flow surface at different times. Now from one and the same sample flow, two essentially similar sample flows can be conducted to the two different analysers 44 and 46 via the connecting parts 43 and 45. In succession to each perforation group 49 constituting a screen-like member, when seen in the flowing direction 53, there is installed a flow stop member 50 in order to advantageously conduct the sample flow to the perforation group 49. The perforation groups 49 constituting the screen-like member can advantageously be cleaned by means of a cleaning member 47, which comprises nozzles in order to feed cleaning agent to the perforation groups 49, when at least one perforation group 49 is turned, by means of the moving member 48, to a position where at least one perforation group is located above the liquid surface. Now the liquid flow is conducted, via an aperture 51 provided in the control member 41, to the conduit 52 as a bypass flow of the analysers 44 and 46.

What is claimed is:

1. A device for substantially continuously sampling liquid or slurry material, said device including a tubular member having a peripheral wall, first and second opposite ends spaced apart along a longitudinal axis, the tubular member being disposed with the longitudinal axis substantially horizontal for receiving the material to be sampled at said first end, having a first aperture in its peripheral wall, between the first and second ends, and having a second aperture angularly spaced from the first aperture about the longitudinal axis of the tubular member and positioned such that the first aperture is axially between the second aperture and the first end, and the device further including a means for turning the tubular member about its longitudinal axis selectively to either a first position, in which the first aperture is down and liquid or slurry material in the tubular member passes through the first aperture under gravity, and a second position, in which the second aperture is down and liquid or slurry material in the tubular member bypasses the first aperture and passes through the second aperture under gravity.

2. A device according to claim 1, further comprising a dispenser for supplying a cleaning agent for cleaning the tubular member.

3. A device according to claim 1, including a means for sieving material as it passes through the first aperture.

4. A device according to claim 3, further comprising a dispenser for supplying a cleaning agent for cleaning the sieving means.

5. A device according to claim 1, further comprising a screen attached to the tubular member for sieving material passing through the first aperture.

6. A device according to claim 1, wherein said first aperture is one of a plurality of perforations in the wall of the tubular member, said perforations being positioned to allow liquid or slurry material in the tubular member to pass downwards therethrough under gravity when the tubular member is in the first angular position and serving to sieve the liquid or slurry material.

7. A device according to claim 1, wherein the longitudinal axis of the tubular member is inclined to horizontal at an angle up to 10°, the first end being above the second end.

8. A device according to claim 1, wherein the longitudinal axis of the tubular member is inclined to horizontal at an angle up to 3°, the first end being above the second end.

9. A device according to claim 1, wherein the second aperture is in the peripheral wall of the tubular member.

10. A device according to claim 1, wherein the tubular member has an end wall at its second end and the second aperture is in the end wall.

11. A device according to claim 1, wherein the tubular member has a third aperture which is angularly spaced from the first and second apertures and is formed in the peripheral wall of the tubular member, axially between the first and second apertures, whereby the tubular member can be turned to a third position in which the third aperture is down and liquid or slurry material in the tubular member bypasses the first aperture and passes through the third aperture under gravity.

12. A device according to claim 11, wherein the tubular member includes an internal dam positioned axially between the first and second apertures for limiting flow of liquid or slurry material beyond the first aperture when the tubular member is in the first angular position.

13. A device according to claim 11, wherein the tubular member includes an internal dam positioned axially between the third and second apertures for limiting flow of liquid or slurry material beyond the third aperture when the tubular member is in the third angular position.

* * * * *